(12) United States Patent
Schonholz et al.

(10) Patent No.: US 8,932,251 B2
(45) Date of Patent: Jan. 13, 2015

(54) BIOPSY SPACER DEVICE AND METHOD OF OPERATION

(75) Inventors: Steven Michael Schonholz, Warren, MA (US); James C. McKeon, Longmeadow, MA (US); Glenn E. Vallee, Westbrook, CT (US); Christopher Baltazar, Wilbraham, MA (US); Brian Kozniewski, Belchertown, MA (US); Stephen Lauzon, New Bedford, MA (US); Teresa Mitchell, Commack, NY (US); Yah Laetitia Sangne, Chicopee, MA (US); Robert T. T. Gettens, Longmeadow, MA (US)

(73) Assignee: Western New England University, Springfield, MA (US)

( * ) Notice: Subject to any disclaimer, the term of this patent is extended or adjusted under 35 U.S.C. 154(b) by 101 days.

(21) Appl. No.: 13/416,459

(22) Filed: Mar. 9, 2012

(65) Prior Publication Data

US 2012/0238953 A1  Sep. 20, 2012

Related U.S. Application Data

(60) Provisional application No. 61/451,187, filed on Mar. 10, 2011.

(51) Int. Cl.
| A61M 29/00 | (2006.01) |
| A61B 10/02 | (2006.01) |
| A61B 17/02 | (2006.01) |
| A61M 27/00 | (2006.01) |
| A61M 25/10 | (2013.01) |

(52) U.S. Cl.
CPC .............. *A61B 10/02* (2013.01); *A61B 17/0218* (2013.01); *A61M 27/00* (2013.01); *A61M 2025/1054* (2013.01); *A61M 2025/1086* (2013.01); *A61M 2210/1007* (2013.01)
USPC ...................................... 604/96.01

(58) Field of Classification Search
CPC .................. A61N 5/1015; A61N 2005/1003; A61N 5/1002; A61N 2005/1023; A61N 5/1007; A61N 5/1014; A61N 2005/1018; A61M 25/1002; A61M 25/10; A61M 2025/0039; A61M 2025/004; A61M 2025/1054; A61M 31/00; A61M 37/0069; A61M 2025/105; A61B 2017/22051; A61B 1/12136; A61B 17/3415; A61B 17/3468; A61K 51/1282
USPC ...................................... 604/96.01
See application file for complete search history.

(56) References Cited

U.S. PATENT DOCUMENTS

| 5,913,813 A | 6/1999 | Williams et al. |
| 6,036,631 A | 3/2000 | McGrath et al. |

(Continued)

FOREIGN PATENT DOCUMENTS

| EP | 1618924 | 1/2006 |
| WO | 02092162 | 11/2002 |

(Continued)

*Primary Examiner* — Jason Flick
(74) *Attorney, Agent, or Firm* — Cantor Colburn LLP

(57) ABSTRACT

A breast cavity spacer device, such as for use with a percutaneous lumpectomy, is provided. The device includes a body having a projection on one end. The body has a bore extending there through. A catheter is disposed at least partially within the bore. A balloon member is fluidly coupled on one end of the catheter, the balloon member having an elliptical shape.

18 Claims, 8 Drawing Sheets

(56) References Cited

U.S. PATENT DOCUMENTS

| | | | |
|---|---|---|---|
| 6,117,064 A | 9/2000 | Apple et al. | |
| 6,149,575 A * | 11/2000 | Leonhardt | 600/4 |
| 6,413,204 B1 | 7/2002 | Winkler et al. | |
| 7,056,274 B2 | 6/2006 | Apple et al. | |
| 7,404,791 B2 | 7/2008 | Linares et al. | |
| 7,749,150 B2 * | 7/2010 | Kindlein et al. | 600/3 |

| | | | |
|---|---|---|---|
| 2012/0088952 A1 * | 4/2012 | Lubock et al. | 600/7 |

FOREIGN PATENT DOCUMENTS

| | | |
|---|---|---|
| WO | 02102458 | 12/2002 |
| WO | 2004043531 | 5/2004 |
| WO | 2006041733 | 4/2006 |
| WO | 2006065299 | 6/2006 |

* cited by examiner

BIOPSY SPACER DEVICE AND METHOD OF OPERATION

CROSS REFERENCE TO RELATED APPLICATIONS

The present application claims the benefit of U.S. Provisional Application, Ser. No. 61/451,187 filed Mar. 10, 2011, the contents of which are incorporated by reference herein.

BACKGROUND OF THE INVENTION

The subject matter disclosed herein relates to a spacer device for cavities formed during a biopsy and in particular to a spacer device for maintaining a cavity formed during a percutaneous lumpectomy open for later use during radiation therapy.

Percutaneous lumpectomy is a method shown in FIGS. 1-4 that is used by physicians to diagnose breast and treat cancer. One procedure uses a stereotactic system involving a procedure platform or table that supports the patient and maintains the patient's breast 20 in a fixed location. The system includes an x-ray imaging device and a three-dimensional positioning system. X-ray images of the breast 20 are take at three locations relative to the axis of the table to identify the location of a tumor or area of interest 22 by the clinician. The coordinates of the tumor 22 are utilized by the three-dimensional positioning system to guide a "wand" or needle 24 to the area of interest.

The physician makes an incision location 26 and inserts the needle 24. The physician controls the progression of the needle 24 into the incision 26. Once the needle 24 is in the proper location, a device 28 on the end of the needle 24 deploys a plurality of cauterizing filaments 30 that capture the area of interest 22 and cauterize the remaining tissue. With the area of interest 22 captured, the needle 24 is removed. The removal of the area of interest 22 leaves an elliptically shaped cavity 32 and an insertion track 34 in the breast 20.

Following the biopsy procedure, there may be a period of up to four days while the specimen 22 is evaluated by a pathologist to determine if the tumor is cancerous and if it has been completely excised with clear margins. If it is determined that all of the tumor has not been removed, the physician makes a second incision to remove additional tissue. Once all of the tumor has been removed, a third incision is made for the insertion of a brachytherapy ballon that is used for radiation treatments.

While existing devices and methods of diagnosing and treating breast cancer are suitable for their intended purposes, the need for improvement remains in particular in reducing the number of incisions and in the placement of the brachytherapy balloon.

BRIEF DESCRIPTION OF THE INVENTION

According to one aspect of the invention, a cavity spacer device is provided. The device includes a body having a projection on one end and having a bore extending there through. A catheter is disposed at least partially within the bore. A balloon member is fluidly coupled on one end of the catheter, the balloon member having an elliptical shape.

According to another aspect of the invention, another cavity spacer device is provided. The device includes a body having a projection on one end, the body configured to couple with the biopsy system, the body having a bore extending there through. A first catheter is disposed at least partially within the bore. A drainage catheter is disposed at least partially within the first catheter. An inflation catheter disposed at least partially within the first catheter. A medicinal catheter is disposed at least partially within the first catheter. A balloon member is disposed on one end of the catheter and in fluid communication with the inflation catheter.

According to yet another aspect of the invention, a method of performing a percutaneous lumpectomy is provided. The method includes making an incision in a patient. An area of interest is excised and removed to form a cavity and an insertion tract. A catheter is provided with a balloon member disposed on one end, the balloon member being in fluid communication with the catheter. The catheter is inserted into the incision. The catheter is moved to dispose the balloon member within the cavity. The balloon member is inflated from a first size to a second size. The catheter is removed and the balloon sealed.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

Figure 1:
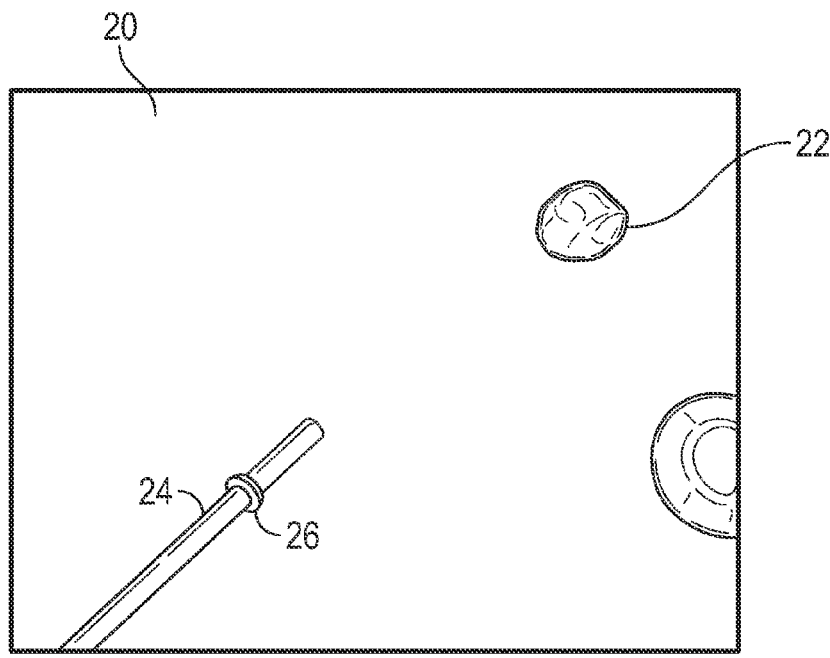
FIGS. 1-5 are illustrations of a prior art biopsy procedure.
Figure 2:
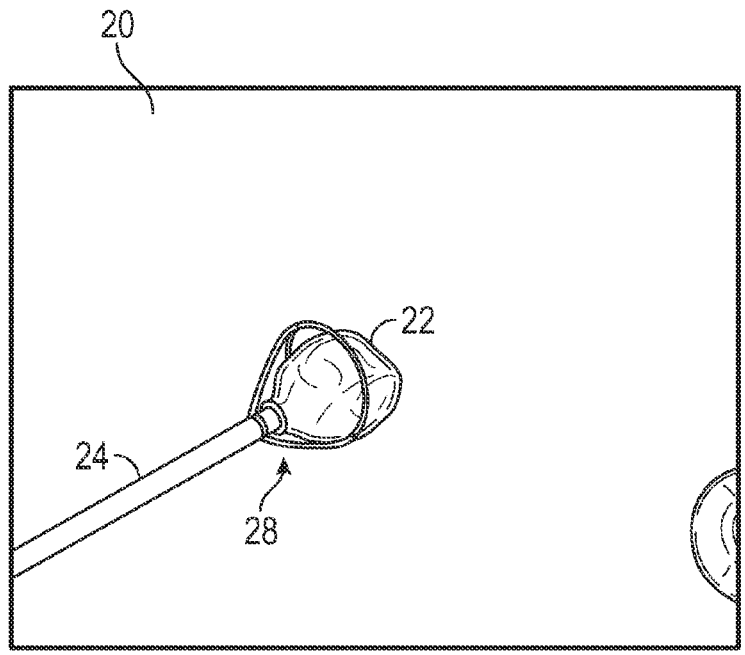
Figure 3:
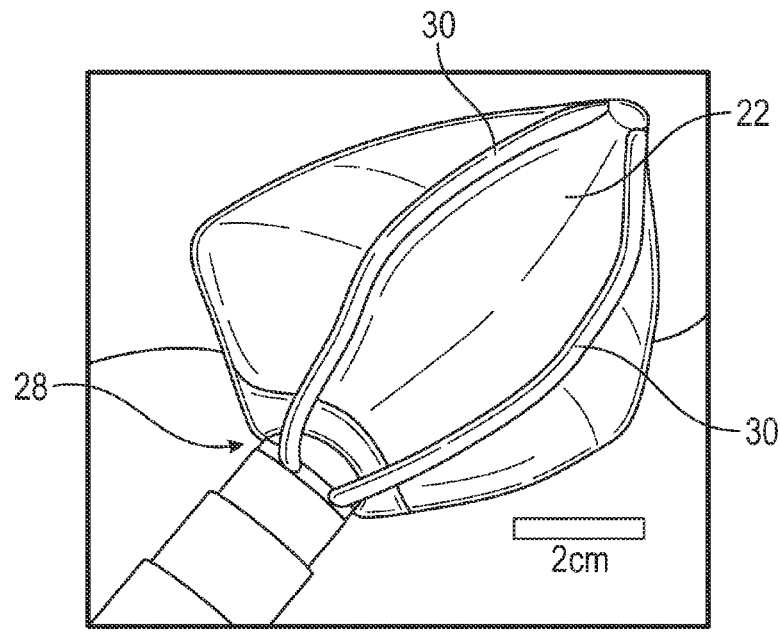
Figure 4:
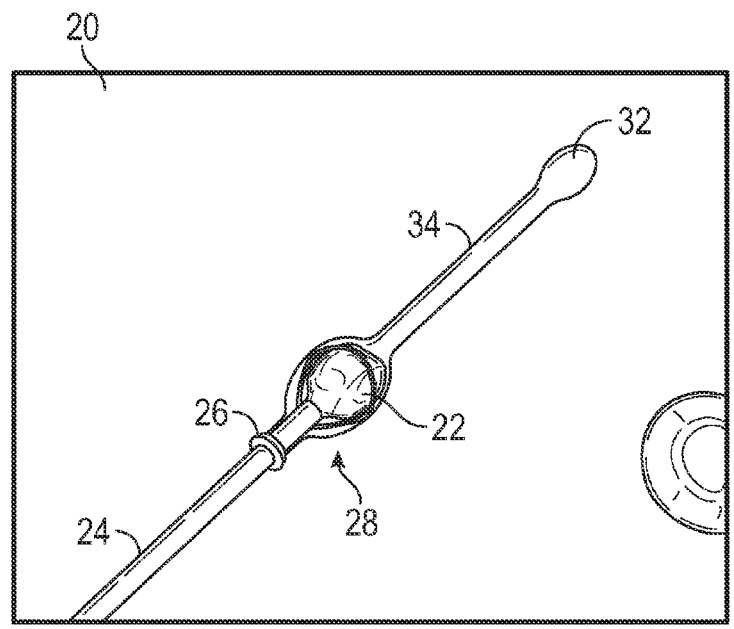
Figure 5:
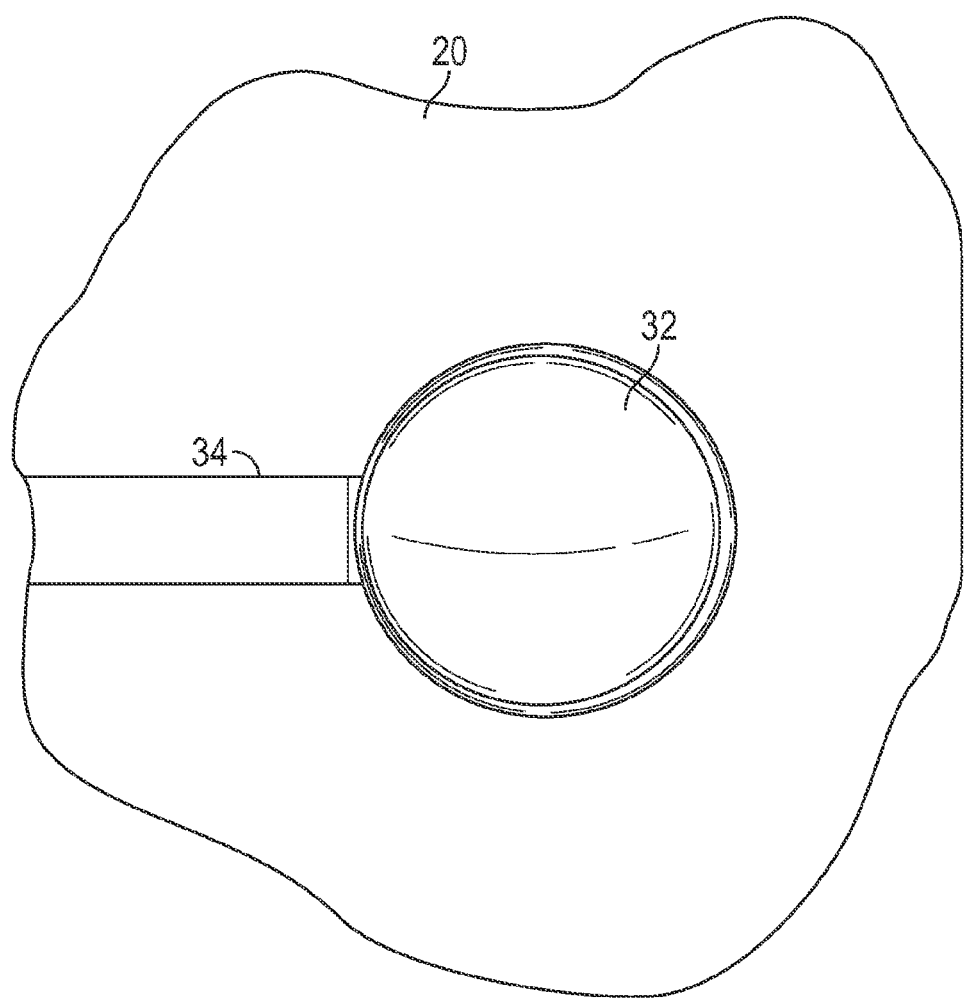
Figure 6:
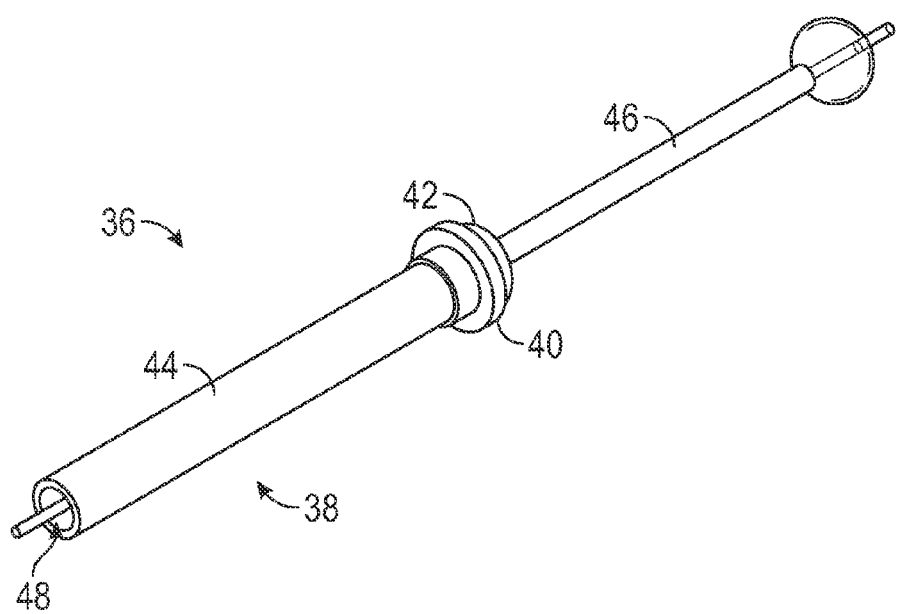
FIG. 6 is a perspective view illustration of a spacer device in accordance with an embodiment of the invention.
Figure 7:
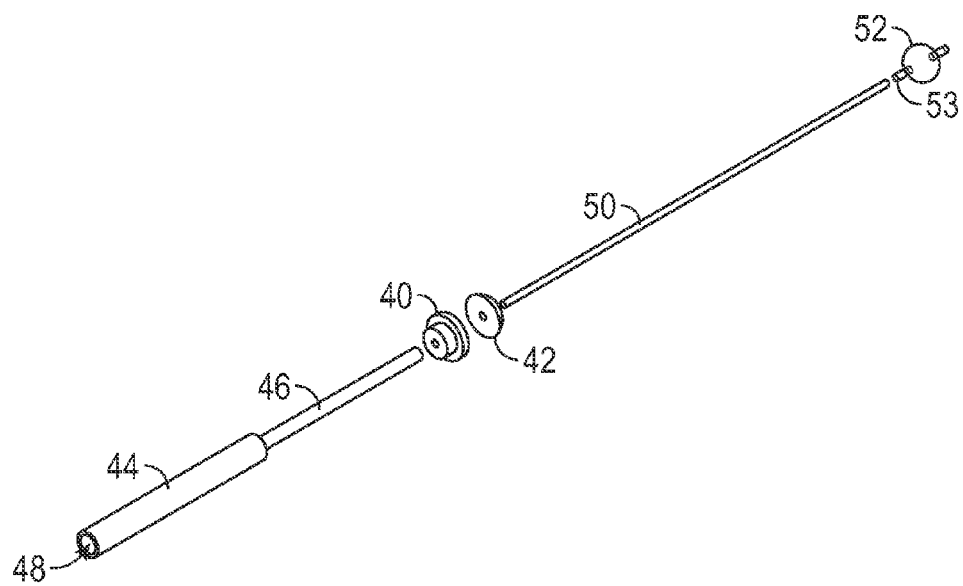
FIG. 7 is an exploded view illustration of the spacer device of FIG. 6.
Figure 8:
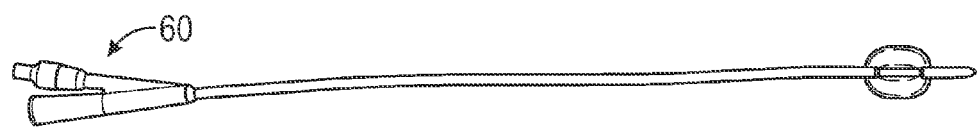
FIG. 8 is a side view of a catheter balloon assembly for use with the spacer device of FIG. 6.
Figure 9:
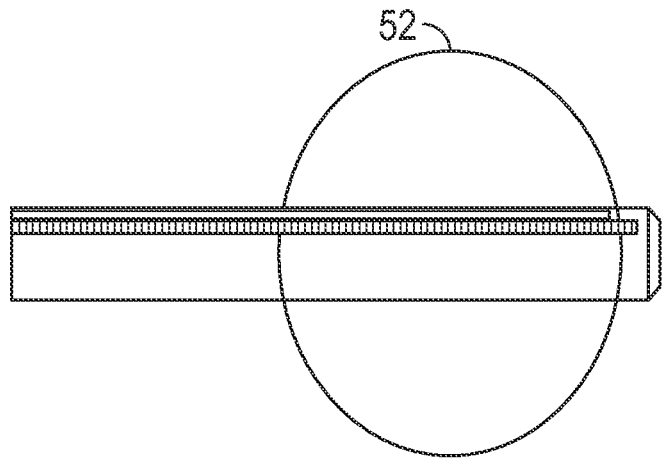
FIG. 9 is a schematic illustration of the balloon end portion of the breast cancer spacer device of FIG. 6; and, FIG. 10 is a sectional schematic illustration of the catheter portion of the spacer device of FIG. 6.

The detailed description explains embodiments of the invention, together with advantages and features, by way of example with reference to the drawings.

DETAILED DESCRIPTION OF THE INVENTION

A percutaneous lumpectomy is a biopsy procedure that removes cancerous tissue and leaves behind an open tract. Embodiments of the present invention provide a breast cavity spacer device that is utilized after the lumpectomy procedure to keep the tract open for the three to four days while the removed tissue is analyzed. The breast cavity spacer device may provide advantages in eliminating or reducing the number of incisions needed to treat the patient. The breast cavity spacer device may provide advantages in allowing radiation treatment to be initiated quickly if the tumor is found to be cancerous. The breast cavity spacer device may provide further advantages allowing a brachytherapy balloon to be placed in substantially the same position as the removed tumor. The breast cavity spacer device may provide yet further advantages in the delivery of medication to the cavity to decrease patient pain or discomfort.

Referring to FIGS. 6-10 an exemplary embodiment of a breast cancer spacer device 36 is shown. The device 36 includes a wand member 38 having a body 44 with a projection 46 extending from one end. The wand member 38 further includes a threaded flange 40 and a holder member 42 disposed adjacent the projection 46. The wand member 38 is configured to interface with the handle of a stereotactic lesion excision system (not shown) that is used for the lumpectomy procedure. In one embodiment, the stereotactic lesion excision system is a MammoTest® Intact® Medical Breast Lesion Excision System manufactured by Siemens AG. The stereotactic system is used to guide the device 36 to the location of the removed tissue.

A bore 48 extends longitudinally through the body 44 and projection 46. The bore 48 is sized to allow a catheter 50 to extend through the wand member 38. The wand member 38 is made from a suitable material such as high molecular weight polyethylene for example. The thread flange 40 is configured to allow the wand member 38 to be secured into the stereotactic system handle while it is being inserted into the breast 20. The holder member 42 keeps the threads in the proper location on the wand member 38 while procedure is being performed.

Figure 10:
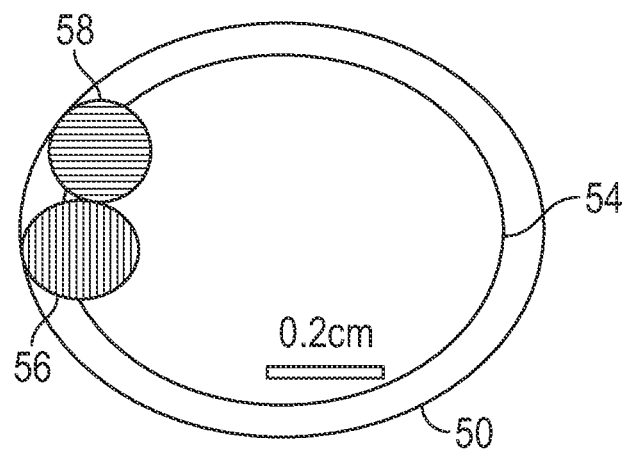

Extending through the bore 48 is a catheter 50. The catheter 50 is a generally thin walled member of sufficient length to allow the physician to extend the catheter through the bore 48 to place a balloon member 52 in substantially the same location where the tumor 22 was excised. In one embodiment, the catheter 50 includes three conduits or catheters for the delivery or extraction of materials from the patient. As shown in FIG. 10, these conduits may include a drainage catheter 54, a medication catheter 56 and a balloon inflation catheter 58. It should be appreciated that this provides advantages in providing a means for inflating the balloon, in the draining of any seroma that may form and in the delivery of medication to ease pain or discomfort. In one embodiment, the catheter 50 may have a manifold 60 (FIG. 8) that bifurcates the catheter to allow multiple internal conduits 54, 56, 58 to be segregated for their intended functions.

The balloon member 52 is arranged on one end of the catheter 50 in fluid communication with the inflation catheter 56. Once the balloon 52 is in the desired location (e.g. the location where the tissue 22 was removed), the balloon 52 is configured to be inflated with saline solution that will keep the cavity 32 open (e.g. will not close due to healing). The balloon 52 is made from a suitable material to withstand the pressures internal to the patient's body. Once the balloon 52 is inflated, the catheter 50 and the wand member 38 are removed. In the exemplary embodiment, the balloon 52 is a self-sealing balloon that allows the catheter 50 to be removed with substantially no loss of pressure. In one embodiment, the balloon 50 includes a tube portion 53 that extends from one side. The tube portion 53 may be pinched by the physician when the catheter 50 is removed. The tube portion 53 may be positioned within the insertion tract 34 to keep the tract 34 open between the time the tissue 22 is removed and subsequent procedures are performed (e.g. 2-4 days). In one embodiment, the balloon member is elliptically shaped and available in three sizes corresponding to the three sizes of brachytherapy balloons. In another embodiment, the balloon member 52 has a water vapor transmission rate of less than 0.01 g/m²/hr.

After the tissue sample 22 is analyzed, the physician will then drain the saline from the balloon member 52 and the balloon member 52 is removed from the cavity 32 and track 34. In one embodiment, the balloon 50 is deflated by draining the saline solution and applying a negative pressure within the interior of the balloon 50. With the balloon and catheter removed, the physician may then use the same incision 26 to excise additional tissue if the tumor was not completely removed, or insert a brachytherapy balloon to initiate radiation treatment. It should be appreciated that the use of the same incision reduces the pain and discomfort for the patient and allows the physician to place the brachytherapy balloon in substantially the same location as where the tumor 22 was removed.

Figure 11:
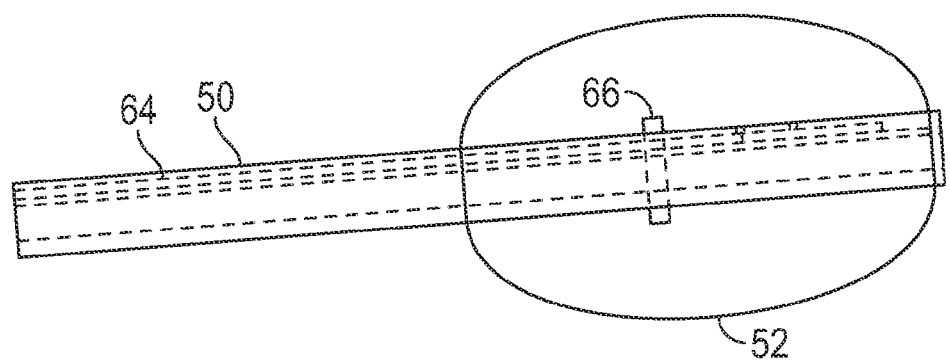
FIG. 11 is a side view of another embodiment of a spacer device
Figure 12:
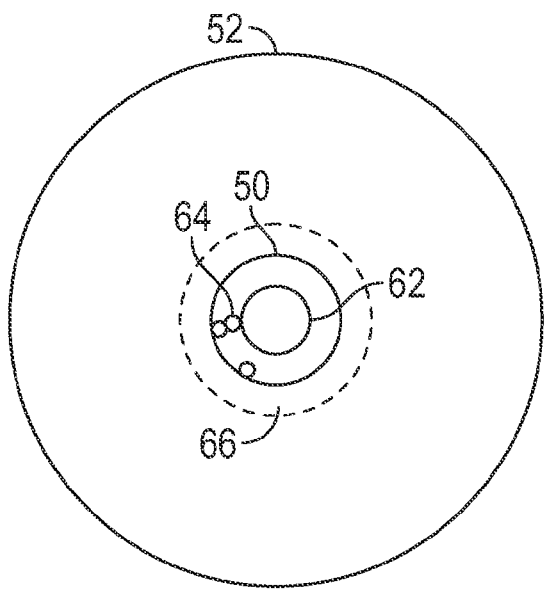
FIG. 12 is an end view of the spacer device of FIG. 11.

Another embodiment of the spacer device 36 is shown in FIGS. 11-12. In this embodiment, the catheter extends through the balloon 52. The catheter includes a first conduit 62 that includes an opening on the end of the catheter 50 to allow for drainage of seroma. The catheter further includes a second conduit 64 that is in fluid communication with a cylindrical projection 66. The cylindrical projection 66 is positioned within the interior of the balloon 52. During operation, once the balloon 52 is in the desired position, a fluid such as saline for example flows through the second conduit 64 and into the interior of the balloon 52. The fluid inflates the balloon 52 to fill the cavity. In one embodiment, the balloon 52 is made from a self-sealing type material that allows the catheter 52 to be removed after the procedure is complete while leaving the inflated balloon 52 in place.

Figure 13:
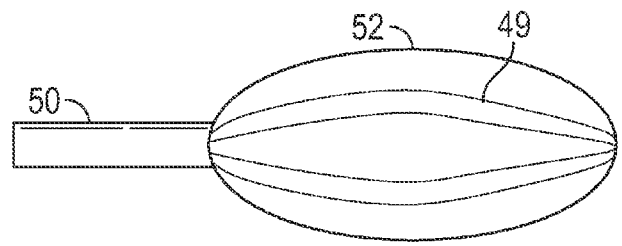
FIG. 13 is a side view of another embodiment of a spacer device.
Figure 14:
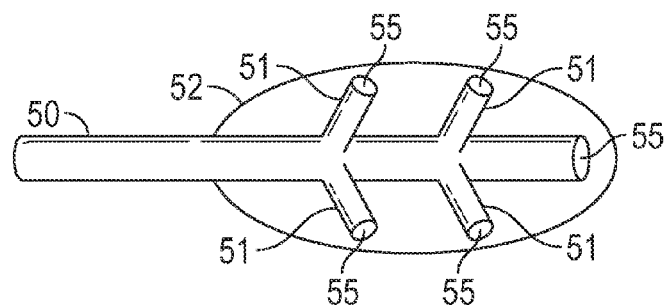
FIG. 14 is a side view of another embodiment of a spacer device.

Another embodiment for a balloon 52 is illustrated in FIG. 13. In this embodiment, the balloon 52 includes one or more ridges 49 disposed longitudinally about the periphery of the balloon 52. The ridges 49 provide additional resistance and provide advantages in preventing the balloon 52 from falling out of the cavity. Yet another embodiment for a balloon 52 and catheter 50 is shown in FIG. 14. In this embodiment, the catheter 50 has a plurality of branch conduits 51 with openings 55 on the end. The openings 55 allow seroma from areas disposed about the cavity. In one embodiment, medication may also be delivered through the openings 55.

Figure 15:
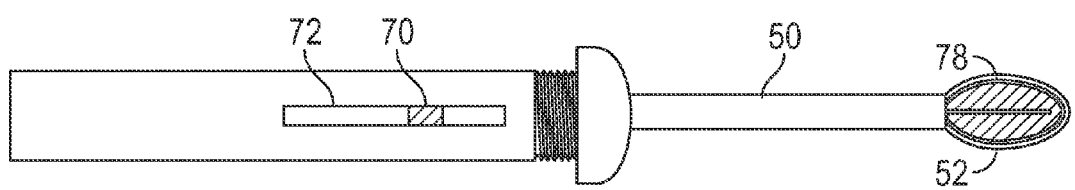
FIGS. 15-16 are side views of another embodiment of a spacer device having a mechanical expansion arrangement.
Figure 16:
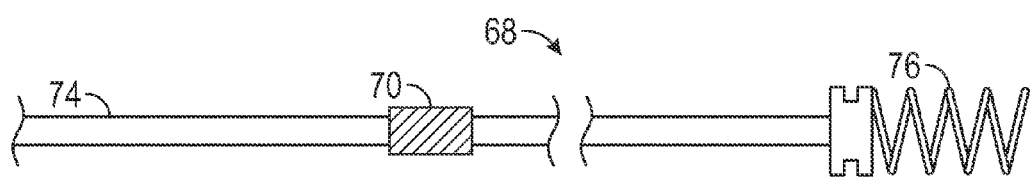

Yet another embodiment of the spacer device 36 is shown in FIGS. 15-16. In this embodiment, the spacer device 36 includes a mechanical expansion assembly 68. The assembly 68 includes a button 70 that slides within a slot 72 in the body 44. The button 70 is coupled to a shaft 74 having a spring 76. On one end of the shaft 74 are a plurality of slats 78 that are movable from a first position inside the catheter 50 to a second position inside the balloon 52. As the button 70 is slid within the slot the slats 78 move from the first position to the second position bend to the desired shape of the cavity as they exit the catheter 50.

It should be appreciated that while embodiments herein describe the use of the spacer device in conjunction with a percutaneous lumpectomy, this is for exemplary purposes and the claimed invention should not be so limited. The invention may also be used with internal radiotherapy, sealed source radiotherapy, curietherapy or endocurietherapy in the treatment of cervical, breast, prostate or skin cancer for example.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A cavity spacer device, the device comprising:
a body having a projection on one end, the body having a bore extending therethrough;
a first catheter disposed at least partially within the bore; and,
a self-sealing balloon member removably and fluidly coupled on one end of the first catheter, the balloon member having an elliptical shape and having a tube portion extending from one side, the tube portion sized to receive the first catheter and having a length sized to extend through a patient insertion tract, wherein the balloon member is configured to move from a first position coupled to the first catheter to a second position removed from the first catheter when the balloon is positioned within a patient, wherein the self-sealing balloon is configured in operation to remain at pressure upon removal of the first catheter and the application of an external force on the tube portion by an operator.

2. A cavity spacer device comprising:
a body having a projection on one end, the body configured to couple with a biopsy system, the body having a bore extending therethrough;
a first catheter disposed at least partially within the bore;
a drainage catheter disposed at least partially within the first catheter;
an inflation catheter disposed at least partially within the first catheter;
a medicinal catheter disposed at least partially within the first catheter; and,
a self-sealing balloon member removably disposed on one end of the first catheter and in fluid communication to receive a saline solution from the inflation catheter wherein the self-sealing balloon is configured to remain at pressure above arterial pressure upon removal of the inflation catheter;
wherein the balloon member is configured to move from a first position coupled to the first catheter to a second position removed from the first catheter when the balloon is positioned within a patient, the balloon member being sealed when the first catheter is removed.

3. A cavity spacer device comprising:
a body having a projection on one end, the body configured to couple with a biopsy system, the body having a bore extending therethrough;
a first catheter disposed at least partially within the bore;
a drainage catheter disposed at least partially within the first catheter;
an inflation catheter disposed at least partially within the first catheter;
a medicinal catheter disposed at least partially within the first catheter;
a self-sealing balloon member removably disposed on one end of the first catheter and in fluid communication to receive a saline solution from the inflation catheter;
a second catheter at least partially disposed within the first catheter; and
a saline source fluidly coupled to the first catheter and configured to expand the balloon member from a deflated state to an inflated state with a saline solution.

4. The device of claim 3 wherein the balloon member has a water vapor transmission rate of less than 0.01 g/m2/hr.

5. The device of claim 4 wherein the balloon member has substantially no pressure loss when the balloon member is moved from the first position to the second position.

6. The device of claim 5 further comprising:
a third catheter disposed at least partially within the first catheter, the third catheter configured to drain the saline solution from the balloon member; and
a fourth catheter disposed at least partially within the first catheter, the fourth catheter configured to deliver a medicine into the balloon member.

7. The device of claim 6 wherein the balloon member includes one or more ridges disposed longitudinally about the periphery of the balloon member.

8. The device of claim 7 wherein the first catheter bifurcates on an end opposite the balloon member to form a manifold.

9. The device of claim 2 wherein the balloon member has a water vapor transmission rate of less than 0.01 g/m2/hr.

10. The device of claim 9 wherein balloon member includes a first end and a second end, the first catheter extending through the first end and second end.

11. The device of claim 10 wherein the first catheter bifurcates on an end opposite the balloon member to form a manifold.

12. A cavity spacer device for a biopsy for use in treating tissue inside a cavity formed by a biopsy, the device comprising:
a body having a projection on one end, the body having a bore extending therethrough;
a first catheter disposed at least partially within the bore;
a second catheter at least partially disposed within the first catheter;
a self-sealing balloon member removably coupled on one end of the first catheter and movable from an attached position to a detached position, the balloon being fluidly coupled to the second catheter to receive a saline solution in the attached position, the balloon member being expandable from a deflated size to an inflated size, the inflated size being sized to fill the cavity; and
wherein the balloon member is configured to move from a first position coupled to the first catheter to a second position removed from the first catheter when the balloon is positioned within a patient, the balloon being sealed when the first catheter is removed, wherein the self-sealing balloon is configured to remain at pressure above arterial pressure upon removal of the first catheter.

13. A cavity spacer device for a biopsy for use in treating tissue inside a cavity formed by a biopsy, the device comprising:
a body having a projection on one end, the body having a bore extending therethrough;
a first catheter disposed at least partially within the bore;
a second catheter at least partially disposed within the first catheter;
a self-sealing balloon member removably coupled on one end of the first catheter and movable from an attached position to a detached position, the balloon being fluidly coupled to the second catheter to receive a saline solution in the attached position, the balloon member being expandable from a deflated size to an inflated size, the inflated size being sized to fill the cavity, wherein the self-sealing balloon is configured to remain at pressure above arterial pressure upon removal of the first catheter; and
wherein the balloon member has a water vapor transmission rate of less than 0.01g/m2/hr.

14. The device of claim 13 further comprising a third catheter at least partially disposed within the first catheter, the third catheter being fluidly coupled to the balloon member to drain seroma from the cavity.

15. The device of claim 14 further comprising a fourth catheter at least partially disposed within the first catheter, the fourth catheter being fluidly coupled to the balloon member to transfer medicine to the cavity.

16. The device of claim 13 wherein the balloon member includes a tube portion on one end, the first catheter passing into the balloon member through the tube portion.

17. The device of claim 12 wherein the first catheter further includes a first conduit extending through the end of the first catheter.

18. The device of claim 17 wherein the first catheter includes:
- a cylindrical portion positioned within the balloon member and extending about the outer wall of the first catheter; and
- a second conduit positioned within the wall and fluidly coupled to the cylindrical portion.

\* \* \* \* \*